United States Patent [19]

Brown et al.

[11] Patent Number: 4,910,227
[45] Date of Patent: Mar. 20, 1990

[54] HIGH VOLUMETRIC PRODUCTION OF METHANOL IN A LIQUID PHASE REACTOR

[75] Inventors: Dennis M. Brown, Allentown; John J. Lewnard, Emmaus; Pradip Rao; Robert F. Weimer, both of Allentown, all of Pa.

[73] Assignee: Air Products and Chemicals, Inc., Allentown, Pa.

[21] Appl. No.: 255,935

[22] Filed: Oct. 11, 1988

[51] Int. Cl.$^4$ .............................................. C07C 27/01
[52] U.S. Cl. ..................................................... 518/700
[58] Field of Search ......................................... 518/700

[56] References Cited

U.S. PATENT DOCUMENTS

| | | | |
|---|---|---|---|
| 4,031,123 | 6/1977 | Espino et al. | 260/449.5 |
| 4,567,204 | 1/1986 | Mednick et al. | 518/700 |
| 4,628,066 | 12/1986 | Bonnell et al. | 518/700 |

OTHER PUBLICATIONS

Shah et al., AICHE Journal, vol. 28, No. 3, pp. 353–379, 1982.

*Primary Examiner*—Howard T. Mars
*Attorney, Agent, or Firm*—Keith D. Gourley; James C. Simmons; William F. Marsh

[57] ABSTRACT

The present invention relates to a process for improving reactor volumetric productivity in the production of methanol wherein a synthesis feed gas stream containing hydrogen and carbon oxides is contacted with a catalyst slurry containing greater than about 25 wt % of a powdered copper-containing catalyst having a porosity of from about 30% to 70%. Volumetric productivity is maximized in the process by controlling a single parameter, gas holdup, wherein holdup is maintained within the range of about 14% to 26%.

11 Claims, 3 Drawing Sheets

HIGH VOLUMETRIC PRODUCTION OF METHANOL IN A LIQUID PHASE REACTOR

TECHNICAL FIELD OF THE INVENTION

The present invention relates to a process for the high volumetric production of methanol from a synthesis gas comprising hydrogen and carbon oxides.

BACKGROUND OF THE INVENTION

Increased demand in the marketplace for methanol production has led to a search for efficient alternatives to conventional gas phase processes. One alternative is a liquid phase methanol process wherein methanol is produced by contacting a synthesis gas comprising hydrogen and carbon oxides with a catalyst in the presence of an inert liquid. Typically, the synthesis gas is bubbled through the catalyst/liquid mixture wherein a portion of the $H_2$, $CO_2$ and/or CO is converted to methanol.

In contrast to conventional gas phase processes using packed-bed reactors which are loaded with up to 70 vol % catalyst, slurry concentration for liquid phase processes is typically limited to the range of 20 to 45 wt % or 10 to 30 vol % based on the volume of catalyst per volume of reactor. Consequently, known processes for producing methanol in the liquid phase require larger and more expensive reactors than required in conventional processes in order to produce the same methanol production rate.

Representative of processes for forming methanol in the liquid phase is U.S. Pat. No. 4,031,123 which discloses a process for the production of methanol from a feed gas containing hydrogen and carbon oxides wherein the feed gas is passed into a reaction zone containing methanol-forming catalyst particles which are suspended in a paraffinic and/or cycloparaffinic liquid having from 6 to 30 carbon atoms. The process is conducted at temperatures from 150° to 400° C. and pressures from about 200 to 10,000 psia.

U.S. Pat. No. 4,567,204 discloses a process for preparing methanol from synthesis gas containing hydrogen and carbon monoxide in a liquid-phase reactor wherein a methanol-forming catalyst is entrained in an inert solvent and the entrained catalyst is contacted with the synthesis gas. The active element of suitable methanol-forming catalysts includes copper, zinc, aluminum, magnesium, zinc, chromium, molybdenum, uranium, tungsten, vanadium and rare earths. The amount of catalyst entrained in the inert liquid ranges from about 5 to 40 wt %.

U.S. Pat. No 4,628,066 discloses a process for increasing the capacity of a gas phase synthesis loop for the production of methanol from a synthesis feed gas wherein the feed gas is initially passed through a liquid phase methanol reactor to convert a portion of the feed gas to methanol. The unreacted feed gas is passed to a gas phase synthesis loop for further conversion and recovery of methanol. Suitable catalysts include those listed in Col. 4 of U.S. Pat. No. 4,031,123. Average catalyst particle size may range from 0.00002 to 0.25 inches depending on the reactor bed type (trickle bed, liquid fluidized or slurry) and liquid flow rate used in the process. Reactor pressure is maintained between 200 psia and 1,000 psia. Reaction temperatures typically range from between 150° C. to 400° C. with best performance obtained between 230° C. and 250° C.

Canadian Pat. No. 1,157,053 also discloses a process for producing methanol in the liquid phase wherein methanol is produced by contacting a synthesis gas comprising hydrogen and carbon oxides with a catalyst in the presence of an inert liquid. Suitable catalysts are in the form of particles having a diameter of less than about 125 microns.

BRIEF SUMMARY OF THE INVENTION

The present invention relates to a process for improving reactor volumetric productivity in the production of methanol wherein a synthesis feed gas stream containing hydrogen and carbon oxides is contacted with a slurry containing greater than about 25 wt % of a powdered copper-containing catalyst having a porosity of from about 30% to 70%. Volumetric producitivity is maximized in the process by controlling a single parameter, gas holdup, wherein holdup is maintained within the range of about 14% to 26%.

Slurries made with the instant catalysts exhibit low viscosity and yield stress which greatly improves reactor performance and allows for use of higher catalyst slurry concentrations than in known processes. Moreover, intra-particle diffusion does not limit catalyst productivity because catalyst particle size is small, i.e., below the size where intra-particle diffusion limitations exist.

Methanol-forming catalysts suitable for practicing the process are powdered copper-containing catalysts having catalyst porosity of less than 70%. Typically, such powdered catalysts having the enumerated porosity are prepared such that particle size ranges from about 0.1 to 25.0 microns. In a preferred embodiment catalyst porosity is controlled between about 30% and 70%. The powdered catalyst is introduced into a liquid phase reactor in an amount of from about 25 wt % to 65 wt % based upon the weight of catalyst powder divided by weight of slurry. Suitable reaction solvents include hydrocarbon liquids such as mineral oil, paraffins and cycloparaffins having from fourteen to thirty-six carbon atoms per molecule.

Reactor gas holdup is conveniently controlled by adjusting feed gas flow rate and/or catalyst slurry concentration. Reactor pressure is maintained within the range of from about 200 to 2,500 psia and temperatures ranging from about 210° C. to about 280° C. In a preferred embodiment the process is conducted at a pressure from about 500 to 1,500 psia and a temperature from about 210° C. to about 250° C. The feed gas is introduced into the reactor at a rate of 2,000 to 20,000 standard liter/kg catalysthr. Liquid phase reactors known in the art are suitable for practicing this invention although the process has been found to operate particularly well in a bubble column reactor.

The process of this invention which utilizes catalysts having a porosity of less than 70% and a novel control scheme wherein reactor volumetric productivity is optimized by controlling gas holdup, provides substantially improved reactor efficiency while providing fast, inexpensive, on-line control of the reactor.

DETAILED DESCRIPTION OF THE INVENTION

Figure 1:
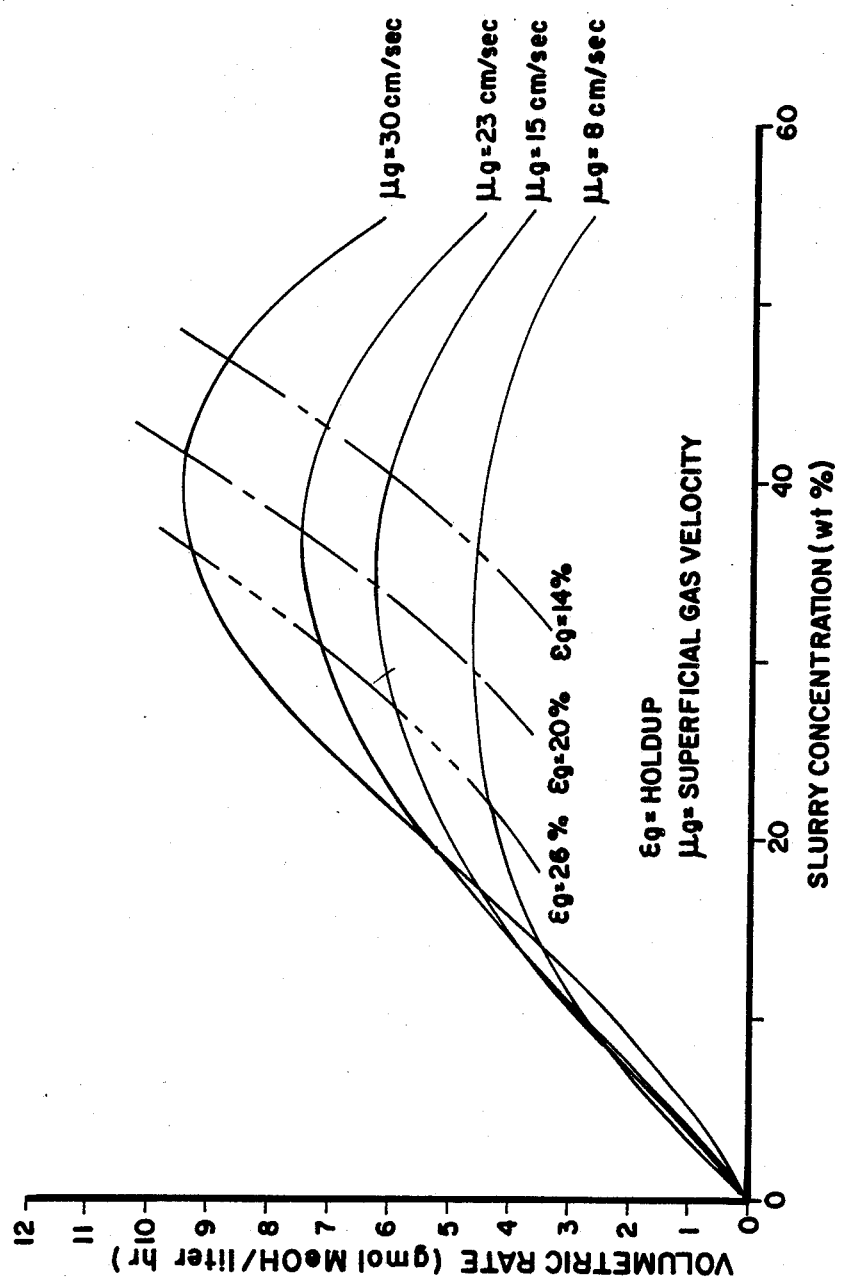
FIG. 1 illustrates reactor volumetric productivity as a function of slurry concentration for a catalyst having a porosity of 68%.

Numerous attempts have been made to overcome problems associated with low volumetric productivity in processes for the liquid phase production of methanol. For example, attempts have been made to increase the productivity of such methanol-forming processes by altering reaction conditions such as temperature and pressure. While an increase in reaction temperature usually increases the rate of reaction, the reversible mechanism of methanol synthesis results in an equilibrium limitation for reactor productivity. Attempts to improve productivity by controlling pressure have also met with similar failure because such productivity gains are often offset by economic penalties associated with processes run under high pressure.

Reactor volumetric productivity in known liquid phase processes for the production of methanol can also be controlled to a limited extent by adjusting the catalyst concentration within the slurry. Maximum slurry concentration is typically limited to about 25 wt % catalyst at which concentration apparent catalyst activity and reactor productivity begin to decrease. Decreased reactor productivity is attributed to unfavorable hydrodynamic conditions for mixing of the feed gas and catalyst slurry and low gas-liquid mass transfer rates within the reaction media. Mass transfer rates and reaction hydrodynamics are sensitive to slurry viscosity and yield stress which increase exponentially with increasing catalyst concentration. Hence, merely adding more catalyst into the liquid solvent benefits the process only at low catalyst concentrations and does not offer a substantial improvement in volumetric productivity.

The instant process for the production of alkanols in a liquid phase or three-phase reactor avoids the loss in apparent catalyst activity typically associated with increased slurry concentration by employing powdered copper-containing catalysts having porosity of less than about 70%. It has been discovered that slurries containing powdered copper-containing catalysts having low porosity exhibit low viscosity and yield stress while maintaining or surpassing intrinsic activity of catalysts known in the art. Therefore, this process provides a means for increasing the effective amount of catalyst in the slurry and maintaining the apparent activity of the catalyst without increasing mass transfer resistance.

Theoretically, this process which utilizes powdered copper-containing catalysts having low porisity could suffer intra-particle mass-transfer limitations typically associated with current gas phase operations which use large catalyst pellets having a diameter in the range of 0.7 to 0.3 cm. However, it has been discovered that copper-containing catalysts having porosity of less than 70%, and preferably between about 30% to 70%, do not suffer from such mass transfer limitations when utilized in the form of a powder.

This invention discloses a process for the high volumetric production of methanol as a product, co-product or reaction intermediate wherein a synthesis feed gas containing hydrogen and carbon oxides (i.e., CO and $CO_2$) is introduced into a reactor containing a slurry of a copper-containing methanol-forming catalyst suspended in a liquid solvent. More particularly, the process involves reacting the feed gas in the presence of a slurry containing greater than 25 wt % of a powdered copper-containing catalyst having a porosity between about 30% and 70%.

Suitable copper-containing catalysts for practicing this invention include those known in the art to produce $C_1$-$C_4$ aliphatic linear and branched alcohols under standard reaction conditions when placed in contact with a feed gas containing hydrogen and carbon oxides. Preferred slurries are prepared by suspending greater than about 25 wt % of the powdered copper-containing catalyst into the liquid solvent. While particle size of the powdered catalyst is not critical, suitable particle size ranges from about 0.1 to 25.0 microns. Particularly preferred are those commercially available catalysts having a porosity of less than 70% and preferably between about 30 and 70%.

In choosing a catalyst for this process, a catalyst and/or its method of preparation should be chosen such that catalyst porosity is reduced to the greatest extent possible without loss in intrinsic catalyst activity. In general, this goal can be achieved by decreasing the average pore size of the catalyst while maintaining the catalyst surface area. Catalysts suitable for practicing this invention are typically reduced in the presence of a hydrogen atmosphere prior to use in the process to maximize catalyst activity. Catalyst porosity values presented herein have been determined by titration to incipient wetness, or alternately, by mercury porosimetry which values are corrected to account for inter-particle void space.

Preferred catalysts are utilized in the powdered form although preliminary investigation suggests that catalysts which are commercially available in pellet form having the enumerated porosity can be pulverized into a powder without a significant detrimental effect on catalyst activity and reactor volumetric productivity. However, caution must be exercised to avoid overheating the catalyst when pulverizing pellets into the preferred powdered form because excessive heat may cause sintering of the catalyst which may detrimentally affect catalyst activity. Preferred catalysts include the copper-/zinc-oxide methanol synthesis catalysts designated as BASF S3-85 and BASF S3-86 which are commercially available in the pellet form from BASF Corporation Ludwigshafen, West Germany.

Whenever possible, the powder precursor of the pellet should be used instead of pulverized catalyst pellets. The lower limit on catalyst porosity is set by diffusion limitations imposed on reactants and products. For copper-containing catalysts having a porosity of less than 30%, intra-particle diffusion rates may reduce the overall effectiveness of the catalyst thereby reducing volumetric productivity.

The term, copper-containing catalyst, as used herein refers to any catalyst containing between about 10 to 90 atomic percent copper. The practice of the present invention is not limited to catalysts containing a particular amount of copper but can be practiced advantageously using those copper-containing catalysts known in the art to produce methanol. This finding is consistent with an article entitled Methanol Synthesis by K. Klier, *Advances in Catalysis,* Vol. 31, p. 243 (Academic Press, Inc., 1983) which states that copper-containing methanol-forming catalysts demonstrate maximum intrinsic activity when catalyst copper content ranges from about 30 to 65 atomic percent although activity was present in catalysts residing outside this preferred range.

The process is operated such that reactor gas holdup is maintained in the range of about 14% to 26%. Reactor gas holdup is defined as the percentage by volume occupied by the feed gas within the volume of slurry within the reactor. An article entitled "Design Parameters, Estimations for Bubble Column Reactors" by Shah et al., AIChE Journal, Vol. 28, No. 3, pp. 353-375, discusses gas holdup in gas-liquid reactions and is specifically incorporated by reference herein.

This process which employs copper-containing catalysts having porosity between about 30% and 70% can be run in conventional liquid phase methanol reactors such as those disclosed in U.S. Pat. No. 4,567,204. Gas holdup can be conveniently measured by placing a nuclear density gauge on the reactor. No modification to the reactor is required to accept the nuclear density gauge.

It has been discovered that reactor volumetric productivity can be substantially increased by controlling a single parameter, gas holdup. This is useful because maximum reactor volumetric productivity is achieved when gas holdup is maintained within a very narrow range. Independent of the superficial gas velocity and the particular catalyst used in the process, maximum reactor volumetric productivity has been found to occur when gas holdup is maintained between about 14 to 26%.

The following examples illustrate the nature of the process described herein and are not intended to limit the scope of the invention.

EXAMPLE 1

Preparation of Catalyst Slurry

A 25 wt % catalyst slurry was prepared by charging 1,631 kgs (3,597 lbs) of a light mineral oil into a standard slurry preparation tank and blending 545 kgs (1,201 lbs) of BASF S3-85 catalyst powder into the oil. Following the blending operation, the catalyst slurry was transferred into the slurry loop of a bubble column reactor. The slurry was then subjected to an in-situ reduction procedure wherein the reactor temperature was raised to 100° C. at a rate of 50° C./hr under nitrogen atmosphere. Reducing gas (2% $H_2$ in nitrogen gas) was admitted into the slurry loop at a flow rate of 1200 standard liter/kg catalyst-hr. The reactor temperature was elevated to 200° C. at a rate of less than 10° C./hr and maintained at this temperature for at least twelve hours. (At the end of this reduction period hydrogen consumption dropped to nil). The reactor temperature was then increased to 240° C. at a rate of less than 10° C./hr and the temperature was held for one hour to complete catalyst reduction.

EXAMPLE 2

Preparation of Methanol Using a 25 wt % BASF S3-85 Catalyst Slurry

CO-rich synthesis gas (51% CO, 35% $H_2$, 13% $CO_2$, 1% $N_2$) was admitted into the reactor containing a 25 wt % slurry of BASF S3-85 catalyst (as prepared in Example 1) at a gas hourly space velocity (GHSV) of 5000 standard liter/kg catalyst-hr under reaction conditions of 250° C., and 765 psia. Reactor gas holdup was maintained at about 20% by maintaining superficial gas velocity at 9.5 cm/sec. Reactor gas holdup was measured directly by monitoring an on-line nuclear density gauge situated on the reactor.

EXAMPLE 3

Preparation of Methanol Using a 42 wt % BASF S3-85 Catalyst Slurry

A 42 wt % catalyst slurry of BASF S3-85 catalyst in light oil was prepared according to Example 1 with the exception that 1224 kgs (2700 lbs) of BASF S3-85 catalyst powder were blended into 1755 kgs (3869 lbs) of a light mineral oil. Gas holdup was maintained at about 16% by holding the superficial gas velocity at 15 cm/sec. The reaction was run according to the procedure used in Example 2.

EXAMPLE 4

Preparation of Methanol Using a 38 wt % BASF S3-86 Catalyst Slurry

A 38 wt % catalyst slurry of BASF S3-86, a copper-containing catalyst manufactured in powdered form, was prepared in light oil according to Example 1 with the exception that 478 kgs (1050 lbs) of BASF S3-86 catalyst powder were blended with 780 kgs (1720 lbs) of mineral oil. Gas holdup was maintained at 17% by holding the supeficial gas velocity at 9.1 cm/sec.

EXAMPLE 5

Preparation of Methanol Using a 36 wt % BASF S3-86 Catalyst Slurry

The 38 wt % BASF S3-86 catalyst slurry of Example 4 was diluted to 36 wt % by adding mineral oil. Gas holdup was maintained at about 26% by holding the supeficial gas velocity at 15 cm/sec. The reaction was run according to the procedure used in Example 2, except the space velocity was maintained at 10,000 standard liter/kg catalyst-hr.

Table 1 discloses reactor volumetric productivity achieved by the present process employing catalysts prepared according to Examples 1 through 5. Runs 1, 2, 8 and 9 disclose actual results obtained by the process while runs 3–7 disclose results obtained by computer modeling wherein data obtained from Runs 1 and 2 were extrapolated under the same reaction conditions to determine the effect of catalyst porosity on reactor volumetric productivity.

TABLE I

Volumetric Productivity Achieved by Employing CO-Rich Feed Gas, 250° C., 765 psig, 5000 standard liter/kg catalyst-hr

| Run | Catalyst Example | Porosity (%) | Catalyst Slurry (wt %) | Volumetric Productivity (g mol MeOH/liter-hr) |
|---|---|---|---|---|
| 1 | 2 | 68 | 25 | 2.7 |
| 2 | 3 | 68 | 42 | 4.6 |
| 3 | — | 62 | 50 | 5.6 |
| 4 | — | 56 | 53 | 6.3 |
| 5 | — | 50 | 58 | 7.4 |
| 6 | — | 40 | 63 | 8.8 |
| 7 | — | 30 | 65 | 9.8 |
| 8 | 4 | 66 | 38 | 5.1 |
| 9 | 5 | 66 | 36 | *8.1 |

*Run 9 was conducted using a space velocity of 10,000 standard liter/kg catalyst-hr.

Runs 1 and 2 show reactor volumetric productivities achieved by using catalyst slurries prepared with 25 wt % and 42 wt % catalyst, respectively. Run 2 illustrates that the BASF S3-86 catalyst having a porosity of 68% allows for use of up to a 42 wt % catalyst slurry compared to typical maximum slurry concentrations of 25 wt % achieved using typical processes known in the art.

Run 2 also demonstrates that catalysts of the instant process not only allow for high slurry concentration but provide substantially improved volumetric productivity (4.6 versus 2.7 gmol methanol/liter-hr).

Runs 3 through 7 demonstrate that volumetric productivity increases proportionately with decreasing catalyst porosity. Moreover, the amount of catalyst capable of being retained in the slurry substantially increases as catalyst porosity decreases. Run 7 shows that a powdered copper-containing catalyst having a porosity of 30% allows for use of a 65 wt % catalyst slurry which results in volumetric productivity of 9.8 gmol methanol/kg catalyst-hr. Runs 8 and 9 demonstrate the improvement in volumetric productivity achieved by using the BASF S3-86 catalyst which has a porosity of 66%. A particularly high volumetric productivity was achieved in Run 9 wherein the space velocity was increased from 5000 to 10000 standard liter/kg catalyst-hr.

The instant process for producing methanol can be advantageously run at high volumetric production when the slurry contains greater than about 25 wt % of the powdered copper-containing catalysts disclosed herein and the flow rate of synthesis feed gas is controlled to maintain gas holdup within the range of 14 to 26% It has been discovered that the preferred gas holdup is approximately 20% when employing slurries containing greater than about 25 wt % of a powdered copper-containing catalyst. The process can be run without major plant modifications because gas holdup can be monitored by installing a nuclear density gauge on the reactor.

The preferred gas holdup will vary depending upon the porosity of the particular catalyst employed and the catalyst slurry concentration used in the process. For example, the preferred gas holdup is about 20% for a powdered copper-containing catalyst having a porosity of 68% and increases to about 26% for a catalyst having a porosity of about 30%. As previously stated, volumetric productivity can be monitored on-line and process conditions modified as needed to maintain gas holdup in the optimum range for the particular catalyst used in the process.

Figure 2:
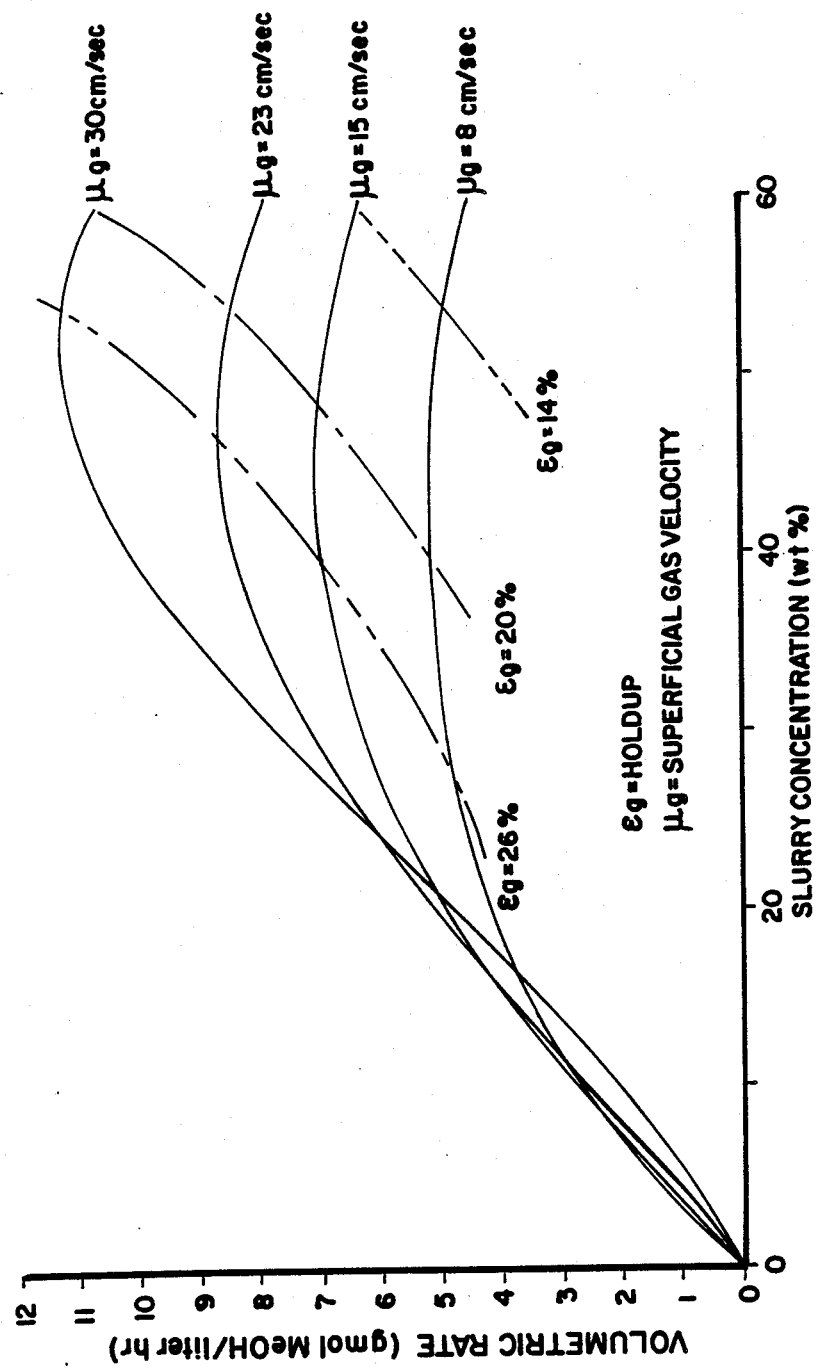
FIG. 2 illustrates reactor volumetric productivity as a function of slurry concentration for a catalyst having a porosity of 40%.
Figure 3:
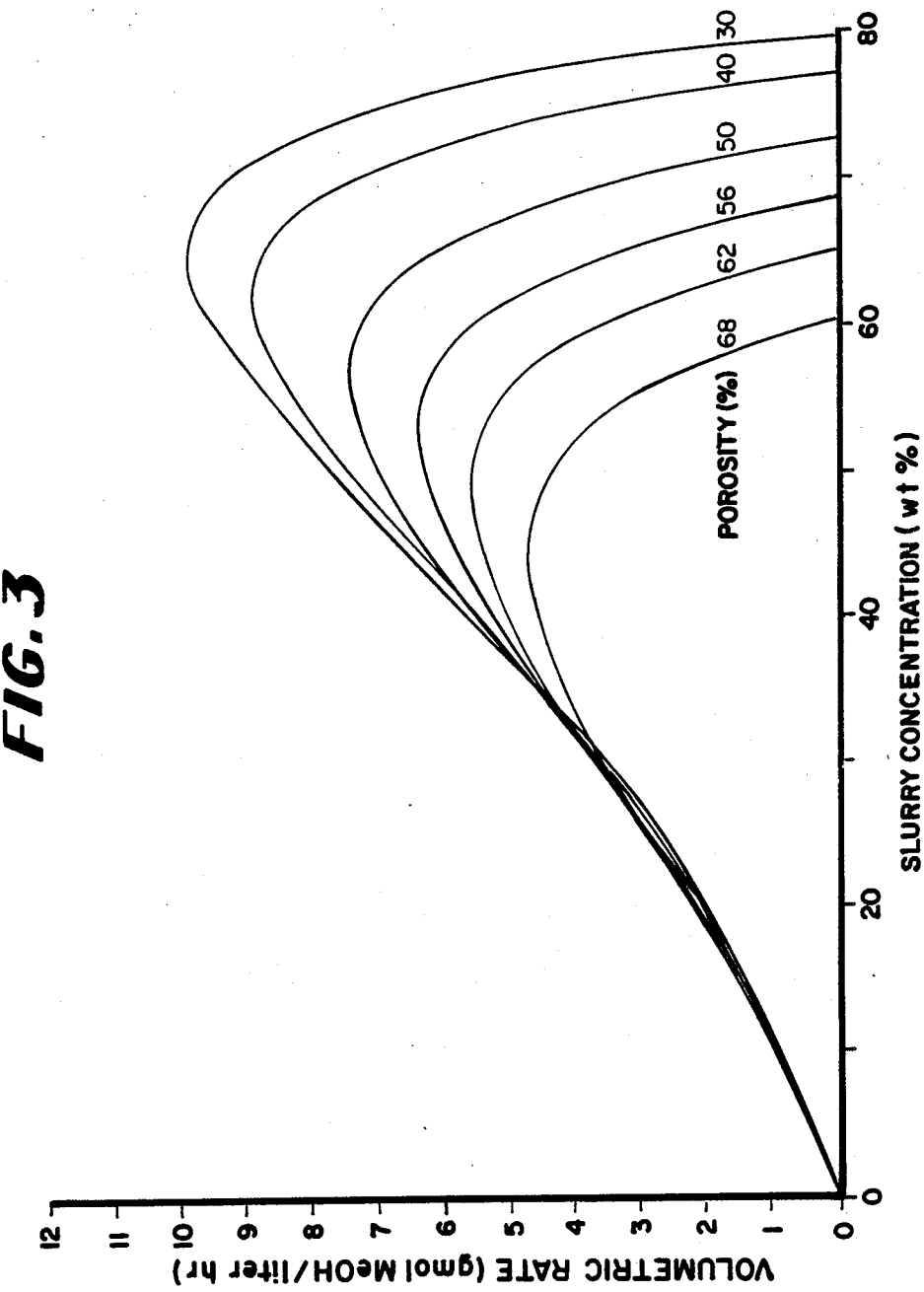
FIG. 3 illustrates the effect of catalyst slurry concentration on reactor volumetric productivity for catalysts having porosities ranging from 30% to 68%.

The effect of catalyst porosity and slurry concentration on reactor volumetric productivity is demonstrated in FIGS. 1 through 3. These Figures were prepared from data obtained by computer modeling wherein the model was constructed using extensive pilot plant data as well as data presented in Table 1. FIG. 1 illustrates volumetric productivity as a function of catalyst slurry concentration. A catalyst slurry of BASF S3-85 was prepared according to Examples 1 and 2 wherein the reduced copper-containing catalyst has a porosity of 68%. Process operating conditions were held constant at 250° C. and 765 psia using a space velocity of 10,000 standard liter/kg catalyst-hr. FIG. 1 demonstrates that maximum volumetric productivity is achieved by controlling gas holdup within a very narrowrange of from about 14 to 26% for a wide range of superficial gas velocities. Consequently, reactor volumetric productivity can be maximized by manipulating slurry concentration and/or preferably, superficial gas velocity, to maintain the gas holdup at close to 20%.

FIG. 2 illustrates volumetric productivity as a function of catalyst slurry concentration for a catalyst having a porosity of 40%. Calculations are based upon reaction conditions of 765 psia, 250° C. and a space velocity of 10,000 standard liter/kg catalyst-hr. Again, the preferred gas holdup is approximately 26% for a catalyst having a porosity of 40%. Operation with gas holdup outside the specified range of 14 to 26% results in decreased volumetric productivity and poor process economics. Without being bound to a particular theory, low volumetric productivity at low holdup values is probably due to low gas-liquid mass transfer rates at the reactant/catalyst interface. Conversely, operation at high gas holdup presumably results in low volumetric productivity because of decreased catalyst inventory as slurry is displaced by feed gas within the reactor.

FIG. 3 illustrates the effect of slurry concentration on process volumetric rate for catalysts having porosities ranging from 30% to 68%. Volumetric productivity varies as a function of catalyst porosity with increasing volumetric productivity being observed as catalyst porosity decreases. Reaction conditions were held constant at 765 psia, 250° C. and a space velocity of 5,000 standard liter/kg catalyst-hr. FIG. 3 also demonstrates that a catalyst having a porosity of 68% has an optimal slurry concentration of 42 wt % and yields a volumetric productivity of 4.6 gmol methanol/liter-hr. In comparison, a catalyst with a porosity of 30% has an optimal slurry concentration of 65 wt % and yields a volumetric productivity of 9.8 gmol methanol/liter-hr.

The claimed process represents a significant improvement over prior art processes because the reactor control scheme requires the monitoring of a single, easily measured variable, the gas holdup. Moreover, gas holdup can be measured on-line with a much faster response rate than volumetric productivity. Gas holdup can be calculated by many techniques known in the art, including monitoring gas-expanded liquid height or density via a nuclear density gauge. The operator can optionally vary the superficial gas velocity or slurry concentration to attain the desired gas holdup.

The superficial gas velocity required to maintain gas holdup will vary with slurry concentration and should be increased with increasing slurry concentration. Suitable superficial gas velocities range from about 3.0 to 50 cm/sec and preferably from 8 to 30 cm/sec for the slurry concentrations disclosed herein. Slurry concentration can also be varied, particularly when the process is run in a reactor designed for catalyst addition and withdrawal. In such cases, slurries can be diluted by adding liquid solvent into the reactor with or without removing some slurry. Alternately, more catalyst can be added to the reactor to increase slurry concentration.

Although this invention is a process for production of methanol, the benefits obtained from using catalysts having decreased porosity and controlling the volumetric productivity by maintaining gas holdup within a narrow range extend to other processes conducted in liquid phase or three-phase reactors. An example of such processes is the Fischer-Tropsch synthesis of hydrocarbons from synthesis gas. The present process can be easily adapted to produce linear and branched aliphatic alkanols having from two to four carbon atoms such as ethanol, propanol, isopropanol and the isomers of butanol.

As stated earlier, volumetric productivity is a function of the total amount of catalyst in the reactor and the apparent activity of the catalyst. The total amount of catalyst in the reactor is greatest with low holdup since very little catalyst is being displaced by feed gas. However, low holdup is also associated with low mass transfer rates since gas-liquid interfacial area is proportional to reactor gas holdup. Consequently, the apparent activity of the catalyst declines with decreasing holdup. Results show these two effects balance to give optimal volumetric productivities when gas holdup is maintained from about 14% to 26% for a wide range of operating conditions. Consequently, the operator can control reactor volumetric productivity by adjusting slurry concentration and/or superficial gas velocity to maintain the maximum gas holdup.

Catalysts having low porosity also permit operation with much more concentrated slurries than previously used. Slurry concentrations in excess of 40 wt %, as discussed herein for production of methanol in the liquid phase are unknown in the art. For example, U.S. Pat. No. 4,562,204 discloses an upper limit on slurry concentration of 40 wt % and states that higher catalyst loadings do not enhance productivity due to decreased mass transfer rates and decreased reaction driving force. Based upon these teachings, it is surprising that this process allows for use of slurry concentrations in excess of 40 wt % and operation with catalyst slurries of up to 65 wt %. The previous limitations on catalyst slurry concentration can be exceeded by this process wherein catalysts having low porosity are employed under controlled gas holdup. Operation of such concentrated slurries provides significantly increased volumetric productivity compared to known processes for the liquid-phase production of methanol.

Having described the present invention, what is now deemed appropriate for Letters Patent is set out in the following appended claims:

What is claimed is:

1. In a process for the production of alkanols as a product, co-product or intermediate in a liquid phase reactor wherein a feed gas containing hydrogen and carbon oxides is reacted in the presence of a catalyst slurry comprising a solid phase catalyst suspended in a liquid solvent under sufficient temperature and pressure to effect reaction between said hydrogen and carbon oxides to form said alkanol and then removing said alkanol, the improvement for maximizing reactor volumetric productivity which comprises:
    (a) utilizing a catalyst slurry having greater than about 25 wt % of a powdered copper-containing catalyst having a porosity of between 30% and 70%; and
    (b) passing said feed gas into said slurry at a rate such that gas holdup is maintained between about 14% to 26%

2. In a process for the production of methanol as a product, co-product or intermediate in a liquid phase reactor wherein a feed gas containing hydrogen and carbon oxides is reacted in the presence of a catalyst slurry comprising a solid phase catalyst suspended in a liquid solvent under sufficient temperature and pressure to effect reaction between said hydrogen and carbon oxides to form said methanol and then removing said methanol, the improvement for maximizing reactor volumetric productivity which comprises:
    (a) utilizing a catalyst slurry having greater than about 25 wt % of a powdered copper-containing catalyst having a porosity of between 30% and 70%; and
    (b) passing said feed gas into said slurry at a rate such that gas holdup is maintained between about 14% to 26%

3. The process according to claim 2 wherein holdup is maintained between about 19% to 23%.

4. The process according to claim 2 wherein the process is maintained at a pressure from about 200 to 2,500 psia and a temperature from about 210° to about 280° C.

5. The process according to claim 3 wherein the process is maintained at a pressure from about 500 to 1,500 psia and a temperature from about 210° to about 250° C.

6. The process according to claim 2 wherein said liquid phase reactor is an agitated reactor.

7. The process according to claim 2 wherein said liquid phase reactor is a bubble column reactor.

8. The process according to claim 2 wherein said slurry contains about 25 wt % to 65 wt % of said copper-containing catalyst suspended in said liquid solvent.

9. The process according to claim 8 wherein said liquid solvent is a branched paraffin or cycloparaffin having from fourteen to thirty-six carbon atoms per molecule.

10. The process according to claim 2 wherein said feed gas is passed into the slurry containing between about 25 wt % to 65 wt % of the solid phase copper-containing catalyst at a superficial gas velocity of about 8 to 30 cm/sec.

11. The process according to claim 2 wherein the copper-containing catalyst is a copper-/zinc-oxide methanol synthesis catalyst.

* * * * *

UNITED STATES PATENT AND TRADEMARK OFFICE
CERTIFICATE OF CORRECTION

PATENT NO. : 4,910,227

DATED : March 20, 1990

INVENTOR(S) : Brown, et. al.

It is certified that error appears in the above-identified patent and that said Letters Patent is hereby corrected as shown below:

On the title page:

Following the abstract kindly insert -- The Government of the United States of America has rights in this invention pursuant to Contract Number DE-AC22-85PC80007 awarded by the U.S. Department of Energy. --

Signed and Sealed this

Twenty-first Day of May, 1991

Attest:

HARRY F. MANBECK, JR.

Attesting Officer

Commissioner of Patents and Trademarks